(12) United States Patent
Ben-Porath et al.

(10) Patent No.: US 6,987,873 B1
(45) Date of Patent: Jan. 17, 2006

(54) AUTOMATIC DEFECT CLASSIFICATION WITH INVARIANT CORE CLASSES

(75) Inventors: Ariel Ben-Porath, Rehovot (IL); Mark Wagner, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/111,454

(22) Filed: Jul. 8, 1998

(51) Int. Cl.
*G06K 9/00* (2006.01)

(52) U.S. Cl. .................. 382/145; 382/143; 382/144

(58) Field of Classification Search ................ 382/141, 382/144, 145, 147, 149, 142, 143; 250/309, 250/310, 311, 559.46, 223 B; 702/35; 348/127; 700/121
See application file for complete search history.

(56) References Cited

U.S. PATENT DOCUMENTS

| | | | |
|---|---|---|---|
| 4,644,172 A | | 2/1987 | Sandland et al. |
| 4,849,901 A | * | 7/1989 | Shimizu ..................... 700/121 |
| 4,877,326 A | | 10/1989 | Chadwick et al. |
| 4,941,980 A | | 7/1990 | Halavee et al. |
| 4,942,619 A | | 7/1990 | Takagi et al. |
| 5,153,444 A | | 10/1992 | Maeda et al. |
| 5,412,210 A | | 5/1995 | Todokoro et al. |
| 5,591,971 A | * | 1/1997 | Shahar et al. ............... 250/310 |
| 5,594,245 A | | 1/1997 | Todokoro et al. |
| 5,644,132 A | | 7/1997 | Litman et al. |
| 5,699,447 A | | 12/1997 | Alumot et al. |
| 5,761,064 A | | 6/1998 | La et al. |
| 5,777,901 A | | 7/1998 | Berezin et al. |
| 5,801,965 A | * | 9/1998 | Takagi et al. ................. 702/35 |
| 5,814,829 A | | 9/1998 | Broude et al. |
| 5,862,055 A | | 1/1999 | Chen et al. |
| 5,903,342 A | | 5/1999 | Yatsugake et al. |
| 5,960,106 A | * | 9/1999 | Tsuchiya et al. ............ 382/144 |
| 6,047,083 A | * | 4/2000 | Mizuno ....................... 382/141 |

FOREIGN PATENT DOCUMENTS

| | | |
|---|---|---|
| EP | 0 359 838 | 3/1990 |
| WO | WO 97/02465 | 1/1997 |

OTHER PUBLICATIONS

"Electron Beam Pattern Inspection System Using Digital Image Processing:"; Saitoh et al; J.Vac.Sci Technol B. vol. 4, No. 3 May/Jun. 1986—pp. 686-691.

(Continued)

*Primary Examiner*—Vikkram Bali
(74) *Attorney, Agent, or Firm*—McDermott, Will & Emery

(57) ABSTRACT

A method and apparatus is provided for automatically classifying a defect on the surface of a semiconductor wafer into one of, e.g., seven core classes: a missing pattern on the surface, an extra pattern on the surface, a deformed pattern on the surface, a particle on the surface, a particle embedded in the surface, a particle and a deformed pattern on the surface, or craters and microscratches on the surface. The defect may also be further classified into a subclass of arbitrarily defined defects defined by the user or preprogrammed in the apparatus. Embodiments include using a scanning electron microscope (SEM) capable of collecting electrons emitted from a plurality of angular sectors to obtain an image of the defect and a reference image containing topographical and location information, then analyzing this information to classify the defect. As the defects are classified, counts are maintained of the number of occurrences of each type of defect, and an alarm is raised if the defect count in a particular class exceeds a predetermined level. Thus, defects are accurately and reliably classified and monitored to enable early detection and cure of processing problems.

22 Claims, 18 Drawing Sheets

OTHER PUBLICATIONS

"Inspection For Defects of A Mask Containing One- to Submicrometer Patterns Using a Scanning Electron Microscope and Feature Extraction Method"; Y. Goto, et al; J.Vac.Sci. Technol 15 (3)0 May/Jun. 1976; pp. 953-956.

"Studies on an Electron-Beam Mask-defect Inspection System"; Y. Wada et al; J. Vac Sci Technol vol. 19 No. 1 May/Jun. 1981.

* cited by examiner

AUTOMATIC DEFECT CLASSIFICATION WITH INVARIANT CORE CLASSES

FIELD OF THE INVENTION

The present invention relates to a method and apparatus for automatically classifying defects on the surface of an article. The invention has particular applicability for in-line inspection of semiconductor wafers during manufacture of high density semiconductor devices with submicron design features.

BACKGROUND ART

Current demands for high density and performance associated with ultra large scale integration require submicron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

Conventional in-process monitoring techniques employ an "inspection and review" procedure wherein the surface of the wafer is initially scanned by a high-speed, relatively low-resolution inspection tool; for example, an opto-electric converter such as a CCD (charge-coupled device) or a laser. Statistical methods are then employed to produce a defect map showing suspected locations on the wafer having a high probability of a defect. If the number and/or density of the potential defects reaches a predetermined level, an alarm is sounded, indicating that a more detailed look at the potential defect sites is warranted. This technique is known as "total density monitoring" of defects and produces a statistic called the "total defect density".

When the defect density reaches a predetermined level, a review of the affected wafers is warranted. The review process is carried out by changing the optics of the inspection apparatus to a higher resolution, or using a different apparatus altogether. To perform the review, the defect map is fed to the review apparatus and then redetection and review of each suspected site is performed according to the defect map.

In the technique called redetection, the potential defect sites are each compared to a reference site, such as a comparable location on an adjacent, non-defective die on the same wafer, to positively determine the presence of a defect. A more detailed review procedure is thereafter carried out on the individual defect sites, such as scanning with a CCD to produce a relatively high-resolution image, which is then analyzed using pattern recognition techniques to determine the nature of the defect (e.g., a defective pattern, a particle, or a scratch).

Thus, detailed review procedures which classify defects and point to specific corrective action to prevent future defects are typically carried out only after a large number of such defects are likely to have occurred. As a result, such defects remain largely undetected until a considerable number of wafers have been fabricated and have begun to exhibit problems caused by the defects. This late discovery of defects can result in a low manufacturing yield and reduced production throughput.

Furthermore, because the defects are not classified until an alarm is raised, and the alarm indicates only that a certain number of defects has probably occurred, alarms may also be generated when only an acceptably small amount of defects of a serious type have occurred; i.e., there is no way to determine before the alarm is raised whether the potential defects are likely to warrant corrective action.

Moreover, optical devices such as CCDs are limited in their ability to analyze and accurately identify defect types. Firstly, the resolution of their images is limited by the pixel size. Secondly, since they produce only two-dimensional images, they cannot gather a large amount of information regarding the topography of a defect, or whether it lies on the surface or below the surface of the wafer. Thirdly, brightness due to reflection of light from certain types of defects, such as scratches, overwhelms the CCD and may produce false defect counts and false alarms. Thus, the review is generally done manually, with an operator reviewing each suspected site of interest.

Since it has recently been recognized that monitoring classified defect density is preferable to monitoring total defect density, various methods for classification of defects have been introduced. However, the efficiency of these methods is reduced because there is no agreed-upon set of defect classes. Specifically, different semiconductor fabricators consider different defects to be important and, therefore, use different sets of defect classes. Consequently, prior art classification methods are tailored to specific users.

Another problem with prior art defect classification systems is that, because they are tailored to user-specific classes, they require many examples of defect images to be obtained for each defect class prior to becoming operational. Consequently, prior art systems cannot be used during start-up and ramp-up of a production line.

There exists a need to quickly and meaningfully review semiconductor wafers and automatically classify the defects in order to identify processes causing defects, thereby enabling early corrective action to be taken. This need is becoming more critical as the density of surface features, die sizes, and number of layers in devices increase, requiring the number of defects to be drastically reduced to attain an acceptable manufacturing yield.

There also exists a need for a standardized set of classes which correlate to the causes of defects. However, since different process lines may be sensitive to different defects from one to another, there exists a further need for a defect classification system with the flexibility to accommodate the needs of various users.

There exists a further need for an automatic defect classification system which is operable during start-up and ramp-up of a production line and which requires no example defect images to become operable.

SUMMARY OF THE INVENTION

An object of the present invention is to provide a method and apparatus for automatic, fast and reliable classification of defects in semiconductor wafers.

According to the present invention, the foregoing and other objects are achieved in part by a method of automatically classifying a defect on the surface of an article, which method comprises imaging the surface and classifying the defect as being in one of a predetermined number of invariant core classes of defects. The defect may then be classified as being in one of an arbitrary number of variant subclasses of at least one of the invariant core classes, at the option of a user of the present invention.

Another aspect of the present invention is a method of inspecting a defect on the surface of an article, which method comprises acquiring an image of the defect; obtaining a reference image; comparing the defect image and the reference image to produce an estimated defect footprint;

obtaining a magnified defect image; obtaining a magnified reference image; and comparing the estimated defect footprint, the magnified defect image and the magnified reference image to produce a defect footprint.

A still further aspect of the present invention is an apparatus for carrying out the steps of the above methods.

A still further aspect of the present invention is a computer-readable medium bearing instructions for automatically classifying a defect on the surface of an article, the instructions, when executed, being arranged to cause one or more processors to perform the steps of the above methods.

Additional objects and advantages of the present invention will become readily apparent to those skilled in this art from the following detailed description, wherein only the preferred embodiment of the invention is shown and described, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Conventional semiconductor wafer inspection techniques do not provide early detection of serious defects, but rather only indicate that a certain amount of defects of all types have occurred. Furthermore, conventional inspection techniques are not capable of analyzing defects in sufficient detail to provide information which leads to early positive identification of the defect source. The present invention addresses and solves these problems by providing automatic classification of defects into meaningful categories, enabling ready identification of processes causing defects, and enabling early corrective action to be taken.

According to certain embodiments of the methodology of the present invention, after a defect map of a semiconductor wafer has been generated, each defect site and a corresponding known non-defective reference site is imaged by a scanning electron microscope (SEM) to gather and store location and topographical data. This data is then analyzed to classify the defect as being in one of a number (e.g., seven) of invariant core classes of defect, and further classified as being in one of an arbitrary number of sub-classes defined by the user of the invention.

Figure 1:
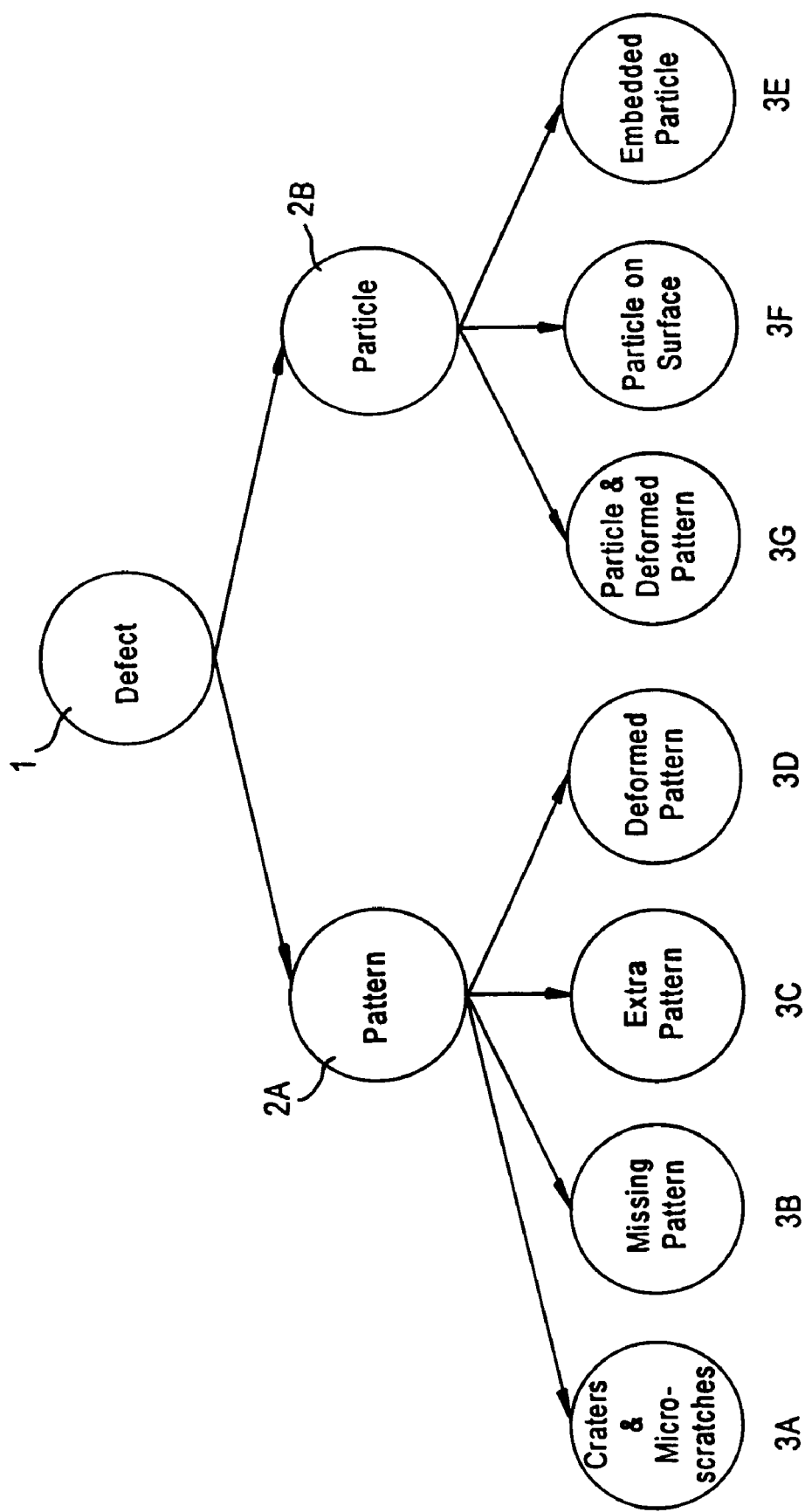
FIG. 1 is a conceptual flow chart of defect classification according to the present invention.

FIG. 1 is a conceptual flow chart of automatic defect classification into core classes performed by the methodology of the present invention. A defect 1 is classified broadly as a pattern defect 2A or a particle defect 2B, and further placed into one of seven exemplary invariant core classes of defects: craters and microscratches on the wafer surface 3A, a missing pattern on the surface 3B, an extra pattern on the surface 3C, a deformed pattern on the surface 3D, a particle on the surface 3E, a particle embedded in the surface 3F, or a particle and a deformed pattern on the surface 3G. Arbitrary sub-classes may include bridging (i.e., short circuiting) between neighboring wiring patterns, a small particle, a large particle, a broken line, a narrow pattern, etc. The defect classification of the present invention facilitates tracing the causes of defects to their source, such as to a particular process step or even to a particular piece of processing equipment.

A typical wafer processing sequence comprises the steps of deposition of a material such as oxide, metal, or nitride, application of photoresist, development of the photoresist, etching and/or polishing, cleaning and, finally, inspection and review. While any parameter of the above-mentioned process steps can introduce defects, most defects are caused by foreign material. The classification of a defect as a particle defect 2B implies that foreign matter is still on the wafer surface. Therefore, if the defect is further classified as an embedded particle defect 3F, this implies that the defect occurred before or during the deposition process, thus pointing out the appropriate corrective action. However, if the defect is classified as a particle on the surface 3E, further analysis of the foreign matter may be carried out, such as by spectroscopy, to identify the material composition of the particle, to trace its origin and thus pinpoint the cause of the defect.

On the other hand, the classification of a defect as a particular type of pattern defect 2A (i.e., crater 3A, missing pattern 3B, extra pattern 3C, or deformed pattern 3D) implies that the foreign material is no longer present on the wafer, and only its effect is visible. Based on the user's knowledge of their fabrication process, the user can conclude, for example, that craters and microscratches 3A were caused by a polishing process, a missing or extra pattern defect 3B, 3C, occurred due to foreign material on top of the photoresist, or a deformed pattern 3D was due to a photolithography problem such as a particle between the wafer and its supporting chuck which caused curvature and loss of focus.

As the defects are classified, counts are maintained of the number of occurrences of each type of defect so that an alarm may be raised if the defect count in a particular class exceeds a predetermined level. Thus, defects are accurately and reliably classified and monitored to enable early detection and cure of processing problems. Based on this type of information, the user of the present invention can set tighter thresholds for defect counts. Additionally, the user can set different alarm thresholds for different defect types depending on their inherent variability (e.g., a particular defect type's tendency to increase when a serious process problem is occurring) or a particular defect's tendency to cause device failure (i.e., its "kill ratio").

Figure 2:
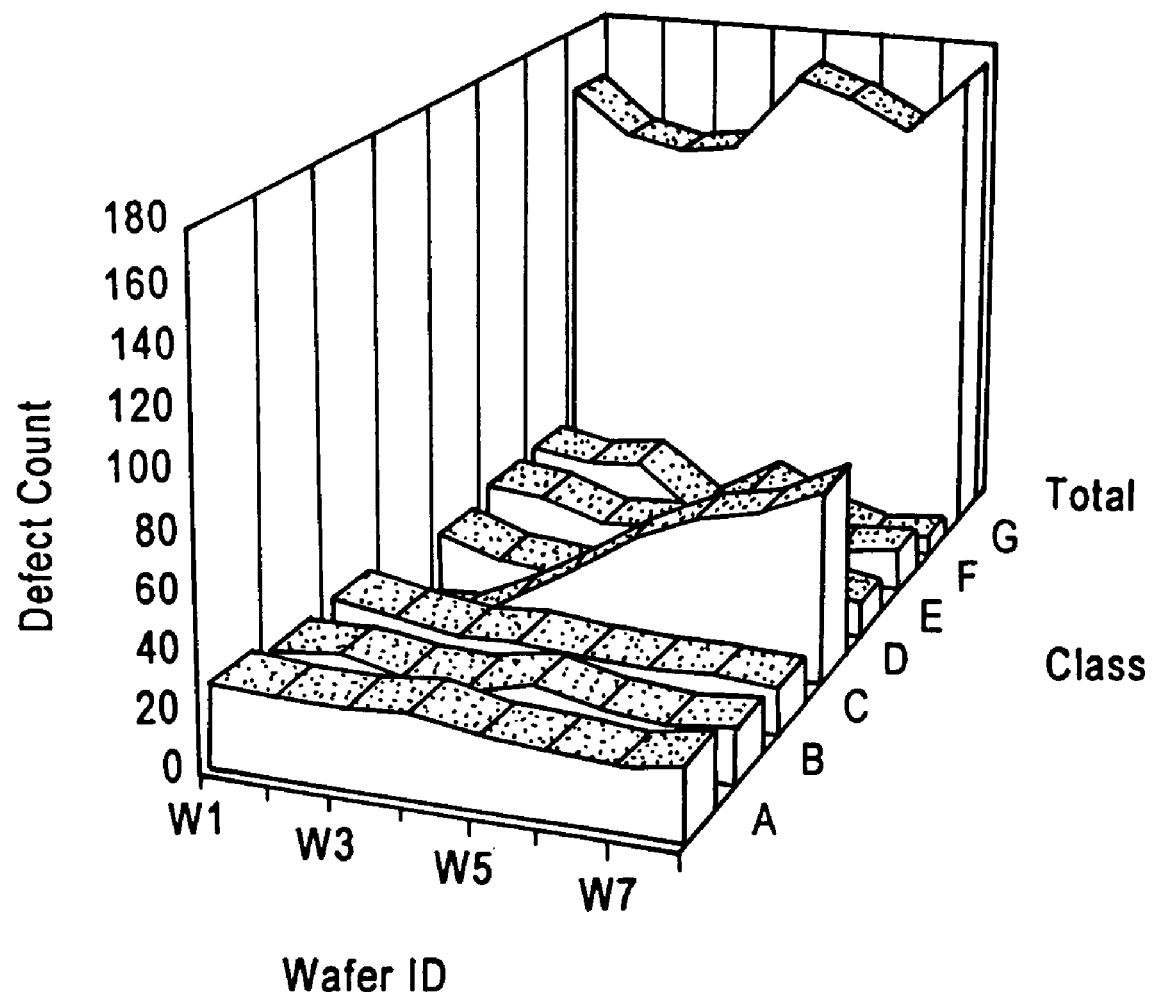
FIG. 2 graphically illustrates defect count by defect class as carried out by the present invention.

The utility of this classified defect density approach is illustrated in FIG. 2, which graphically depicts defect count by defect class A–G for a number of wafers W1–W8. While it can be seen from FIG. 2 that the total number of defects is approximately constant, the occurrence of defect type D is dramatically increasing, though the occurrence of all other defect types is approximately constant. Thus, the user can set the alarm threshold for defect type D lower, if defect D tends to cause device failure, or the user can set the alarm threshold at about 40 defects for all the defect types A–G, in order to detect an increase in any defect type.

Figure 3:
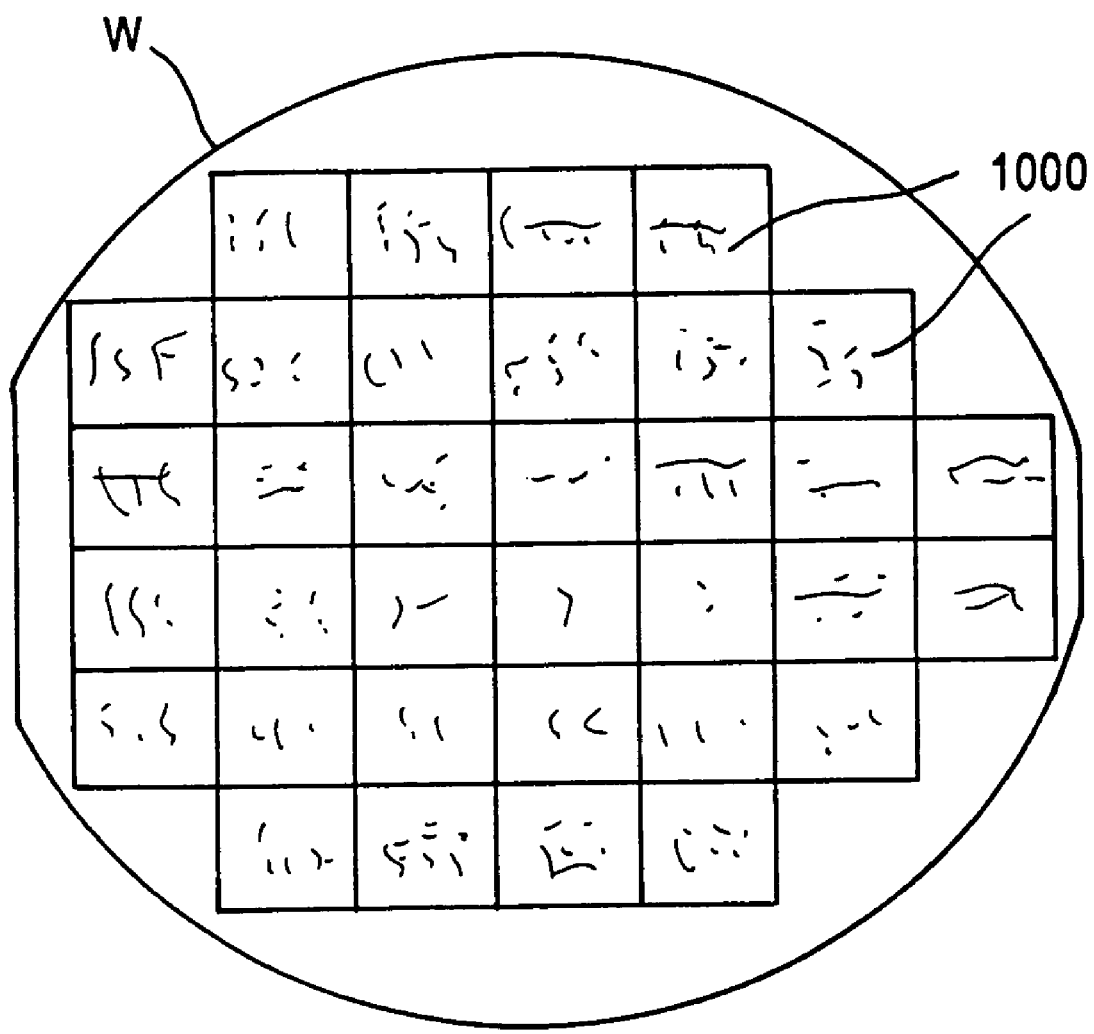
FIG. 3 illustrates a semiconductor wafer to be inspected using the present invention.

An embodiment of the present invention is illustrated in FIGS. 3–14b. As shown in FIG. 3, a semiconductor wafer W to be inspected for defects has a plurality of patterned integrated circuit dies 1000. Initially, a defect map is produced by conventional techniques, such as by scanning the surface of a wafer with a high-speed inspection tool (a CCD, a laser or an SEM may be employed for this purpose), then using statistical methods, typically involving algorithms and/or grey-scale analysis, to identify suspected locations on the wafer having a high probability of having a defect.

Figure 4A:
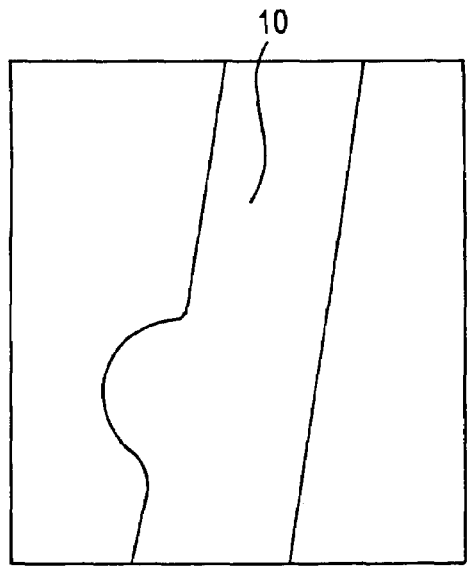
FIGS. 4A–4C are representations of images of a defect to be inspected by the present invention.
Figure 4B:
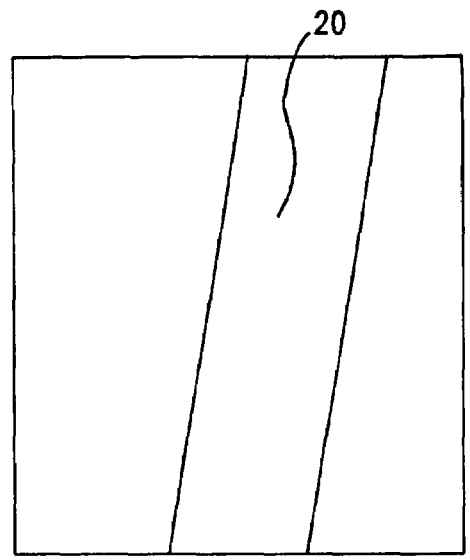
Figure 4C:
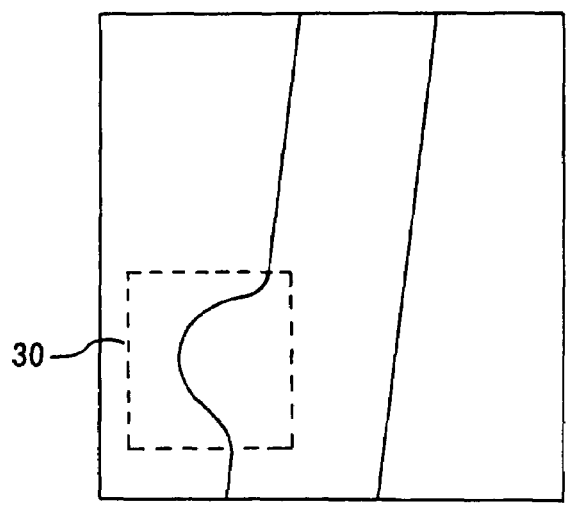

Next, as shown in FIGS. 4A–4C, a redetection procedure is carried out at each suspected defect location to determine the exact location of the defect. A conventional CCD scanner or an SEM may be used to image a pattern 10 at a suspected defect location, which is then compared to a reference pattern 20 at a corresponding location on an adjacent or other die on the same wafer which is not suspected of having a defect. If a difference 30 is found between the suspected defective pattern 10 and the reference pattern 20, the suspected defective pattern 10 is determined to be a defect, and the inventive analysis and classification commences.

Figure 5:
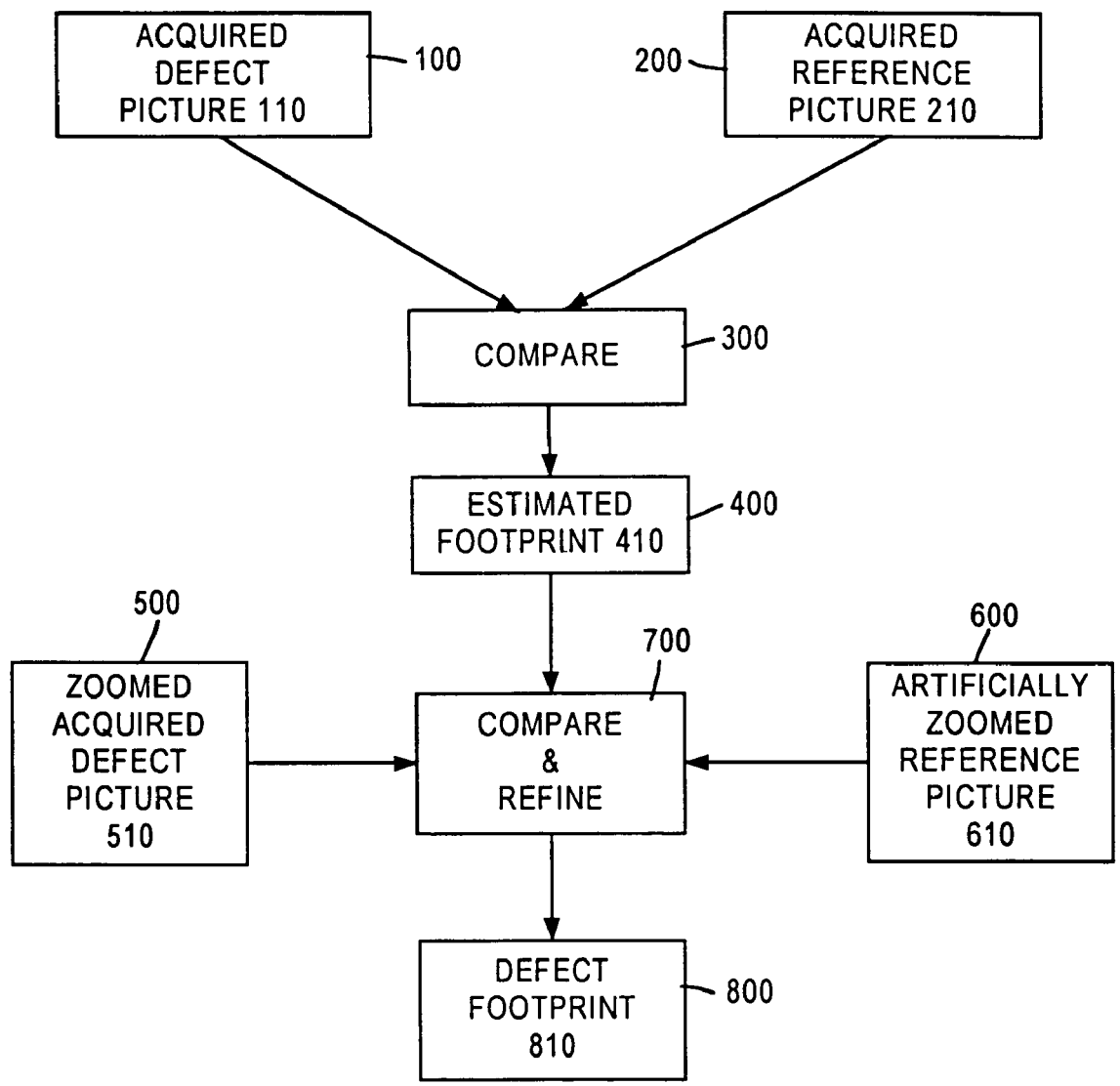
FIG. 5 is a flow chart illustrating sequential steps of a first phase of a method according to the present invention.

FIG. 5 is a flow chart of the first phase of the inventive methodology, which produces a "defect footprint" or detailed image of the defect which is used in all subsequent analysis and classification of the defect. In step 100, a picture 110 of the pattern previously determined to be a defect (i.e., the defective pattern 10 from the redetection procedure) and its surrounding area on the wafer is acquired and stored. All images referred to in the present disclosure and claims are preferably electronically stored (such as on DRAM, magnetic or optical recording media), and all disclosed image manipulation and analysis is preferably automatically performed electronically. Acquired defect picture 110 is preferably produced by an SEM capable of collecting electrons, emitted from a wafer bombarded with electrons, from different angular sectors and generating images of the defect and its surrounding area from multiple perspectives. This type of SEM enables high resolution imaging and measurement of both topographic features and material features of the imaged area. Such an SEM is described in U.S. Pat. No. 5,644,132 to Litman et al. and U.S. Pat. No. 4,941,980 to Halavee et al., the entire disclosures of which are hereby incorporated herein by reference.

A picture 210 of a reference pattern corresponding to the location of the defect pattern is acquired at step 200, at the same magnification. Reference picture 210 can be a common picture for a plurality of defects, or can be a corresponding one for each defect, or can be taken from a computer aided design (CAD) drawing of the die. Reference picture 210 is commonly the reference pattern 20 from the redetection procedure.

The acquired defect picture 110 and the acquired reference picture 210 are compared at step 300 and an estimated defect footprint 410 is produced at step 400. The estimated defect footprint 410 is a contour boundary of the defect; that is, a boundary curve drawn around the defect which includes only the defect. Estimated defect footprint 410 may not be a high-quality picture; i.e., it may contain noise. Therefore, an additional intermediate step is performed, wherein a portion of the acquired defect picture 110 containing the defect (i.e. the portion of acquired defect picture 110 different than the acquired reference picture 210) is magnified at step 500 to produce zoomed acquired defect picture 510. Acquired reference picture 210 is also magnified at step 600, at an area corresponding to the magnified area of acquired reference picture 110. The magnification at step 600 is preferably carried out using an algorithm executed by computer-readable media to reduce the amount of memory required for this step, to produce zoomed reference picture 610.

Figure 6:
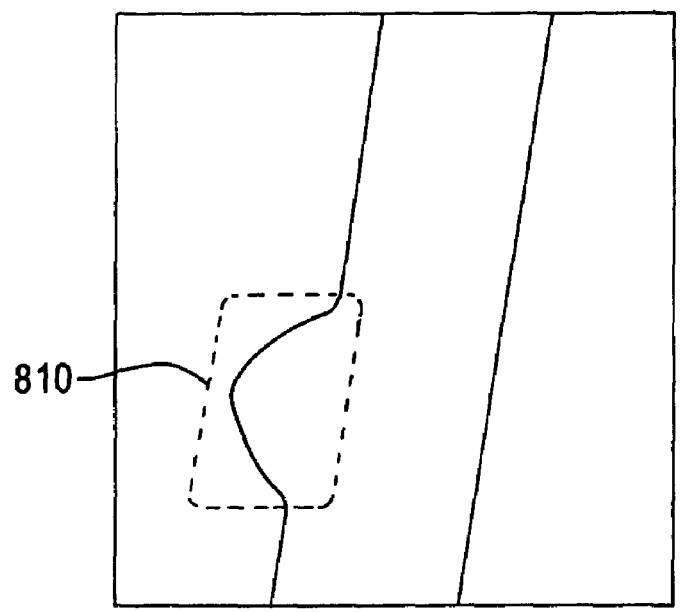
FIG. 6 is a representation of a defect footprint to be analyzed by using the present invention.

At step 700, estimated defect footprint 410, zoomed acquired defect picture 510 and zoomed reference picture 610 are compared and refined to produce defect footprint 810 at step 800. An example of a defect footprint 810 is shown in FIG. 6, and an example of a corresponding zoomed reference picture 610 is illustrated in FIG. 7.

FIGS. 8a–13, depicting a defect and its immediate surroundings, illustrate a second phase of the inventive methodology, which comprises performing a boundary analysis of the defect footprint and reference image to classify the defect in one of seven core classes. FIGS. 14a and 14b are a flow chart of the inventive second phase. The following procedures are performed automatically and are controlled algorithmically, such as by a sequence of instructions on a computer-readable medium.

Referring again to FIG. 7, and to FIG. 14a, the zoomed reference picture 610 is initially analyzed, in a step 1401 called reference segmentation, to identify portions 610a which correspond to a reference pattern and portions 610b which correspond to a background to the reference pattern.

Figure 7:
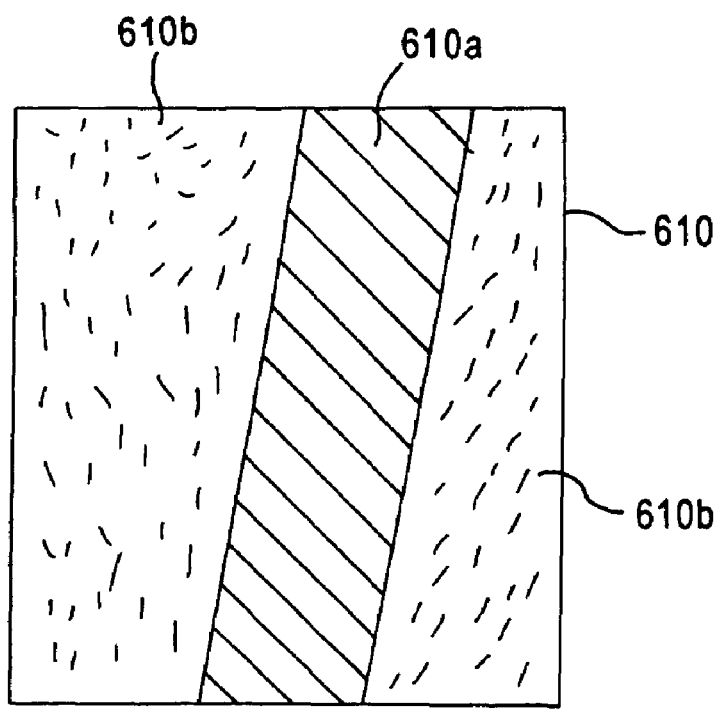
FIG. 7 is a representation of a reference image corresponding to the defect of FIG. 6.
Figure 8A:
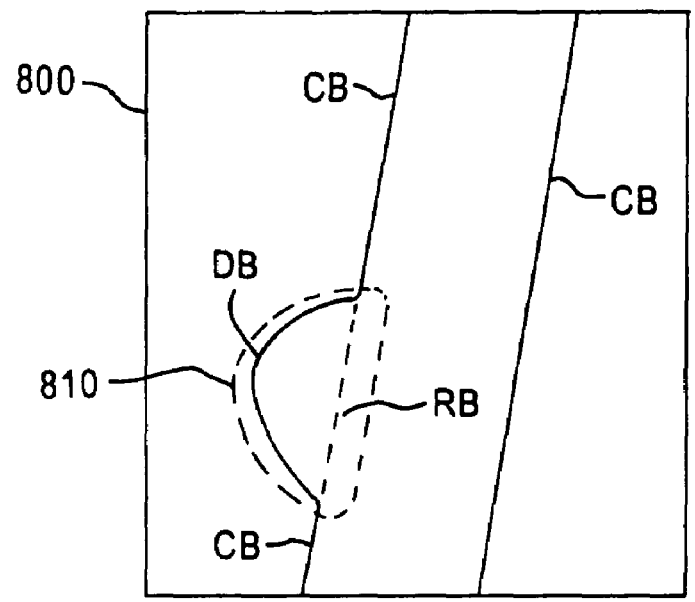
FIGS. 8a–13 are representations of defects to be analyzed using the present invention.

Next, referring to FIGS. 7, 8a, and 14a, common boundaries CB existing in both defect picture 800 and reference picture 610 are identified, defect boundaries DB which exist in the defect footprint 810 only are identified, and reference boundaries RB which exist in the reference picture 610 only (dotted line) are identified in step 1402. This information is analyzed in the following steps, along with reference segmentation data and topographical data, to classify the defect into one of the seven core classes.

Figure 8B:
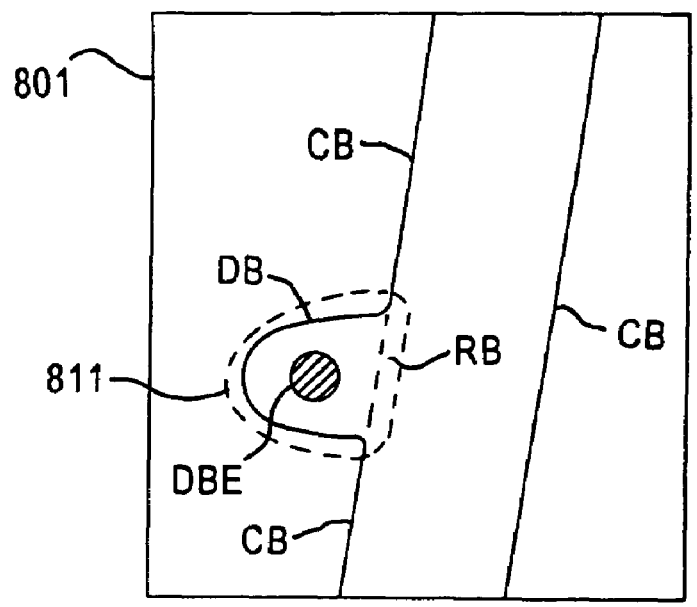
Figure 9:
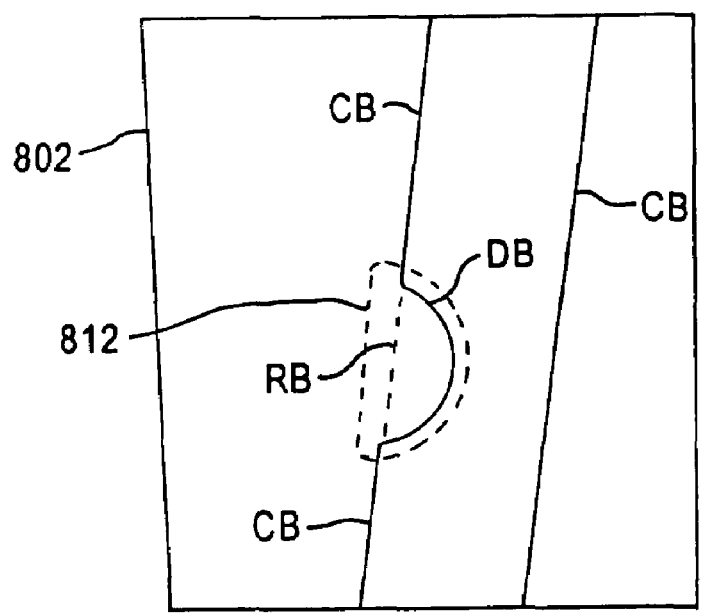
Figure 10:
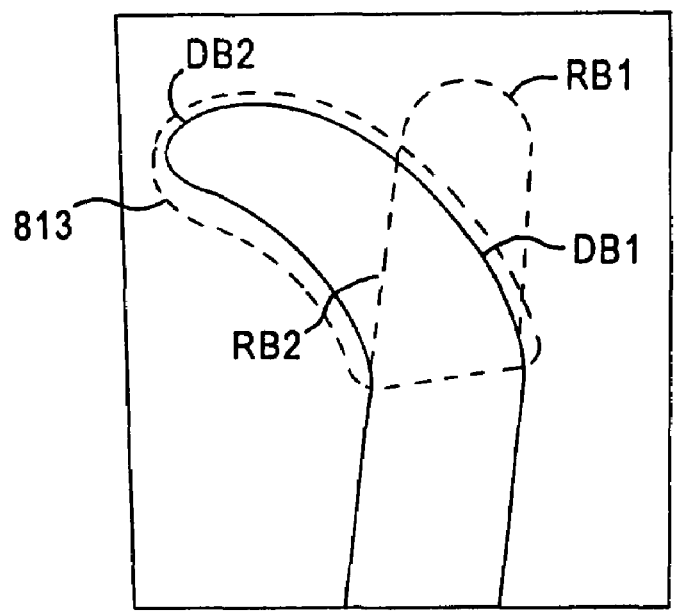

Referring now to FIGS. 8a, 8b, 9, 10 and 14a, in analyzing the defect footprints 810–813, it is determined in step 1403 that defect boundary DB in FIGS. 8a, 8b and 9, and DB1 in FIG. 10 has an open shape (i.e., it is not a loop or polygonal), and that therefore the defect is a pattern defect (step 1404a).

Next, the reference segmentation data is consulted in step 1405, and the defect shown in FIG. 9 is therefore classified in step 1406a as a missing or deformed pattern defect (i.e., pattern data in the reference image is shown as background in the defect image). The defect associated with DB1 in FIG. 10 would also be classified as a missing pattern defect. It is then determined at step 1406b whether another defect boundary (i.e., DB2 in FIG. 10) exists in the defect footprint. At this point, the defect in FIG. 9 is finally classified as a missing pattern defect in step 1406c. However, if DB2 exists, such as depicted in FIG. 10, the reference segmentation data is consulted again in step 1406d, and the defect of DB2 is determined to be an extra pattern. Since DB1 is a missing pattern and DB2 is an extra pattern, the defect of FIG. 10 is finally classified as a deformed pattern defect in step 1406f. In contrast, if DB1 and DB2 were both missing patterns, the defect would be classified as a missing pattern defect at step 1406e.

Referring now to FIG. 14b, if the reference segmentation data shows that the defect is an extra pattern defect at step 1405, as it would for the defects in FIGS. 8a and 8b, defect footprints 810 and 811 are further analyzed for the existence of an additional defect boundary DBE in step 1407. If DBE does not exist, the defect (such as the defect of FIG. 8a) is classified in step 1408a as an extra pattern defect. It is then determined at step 1408b whether another defect boundary such as DB2 in FIG. 10 exists in the defect footprint. If not, the defect in FIG. 8a is finally classified as an extra pattern defect in step 1408c. However, if DB2 were to exist, the reference segmentation data would be consulted again in step 1408d, and the defect of DB2 would be determined to be an extra pattern or a missing pattern. If DB2 was an extra pattern, the defect would be classified as an extra pattern defect in step 1408e, and if DB2 was a missing pattern, the defect would be classified as a deformed pattern in step 1408f.

If DBE exists (such as in the defect of FIG. 8b), topographical data gathered by the SEM is consulted in step 1409 to check the flatness of the area proximal to DBE, and it is determined, if DBE is not substantially flat, that a particle is embedded under the defective extra pattern bounded by defect boundary DB. Consequently, the defect of FIG. 8b is classified in step 1410 as a particle and deformed pattern defect. On the other hand, if the area proximal to DBE is substantially flat, the defect would be classified as an extra pattern defect in step 1411. It would then be determined if another defect boundary DB2 exists in the defect footprint, and the analysis of steps 1408b–1408f would be carried out, as described above.

Figure 11:
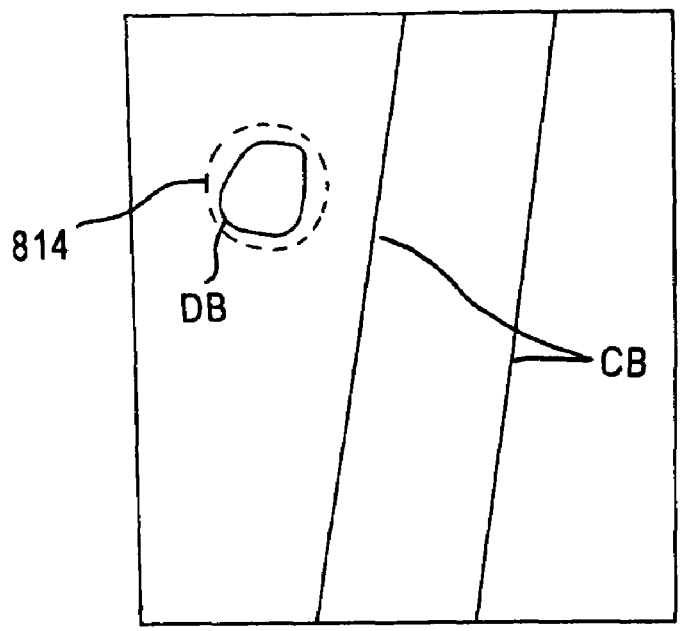

Referring to FIGS. 11 and 14a, if defect boundary DB is determined to have a closed shape in step 1403, as in defect footprint 814, it is considered to be a particle or isolated pattern defect in step 1404b, and it is further determined, in step 1412, whether defect boundary DB intersects the common boundaries CB. If DB does not intersect CB, as shown in FIG. 11, the defect is an isolated defect. However, it could be either an extra pattern or a particle on the surface of the wafer. To determine its classification, the topographical data is consulted in step 1413 to determine the flatness of the area bounded by DB. If the area is substantially flat, the defect is classified as an extra pattern defect in step 1414. If the area is not substantially flat, it is classified as a particle on the surface in step 1415.

Figure 12A:
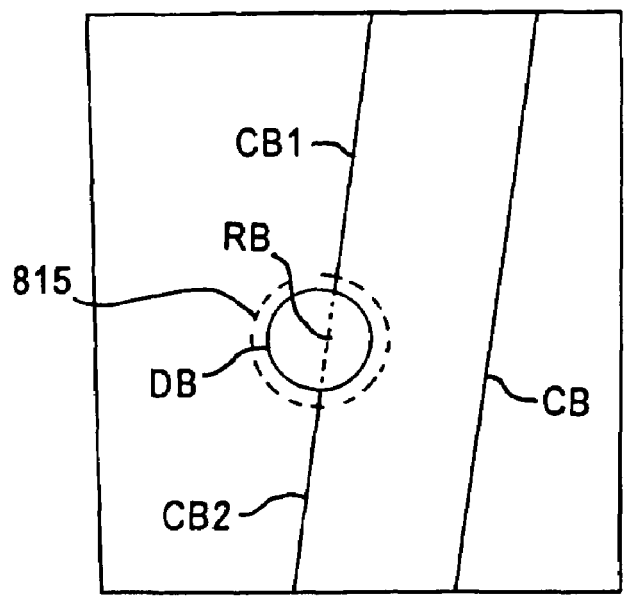
Figure 12B:
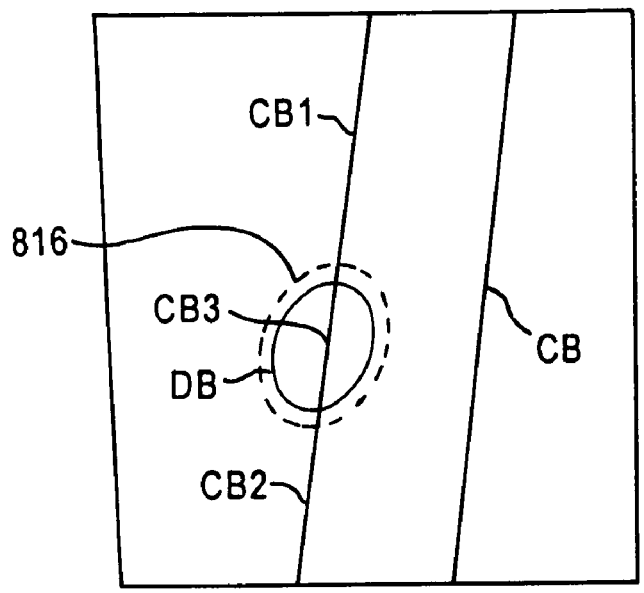

FIGS. 12a and 12b show defect footprints 815, 816 wherein the defect boundary DB has a closed shape, but it would be determined at step 1412 that DB intersects two of the common boundaries CB1 and CB2. If such a determination is made, it is next determined, in step 1416, whether a boundary RB in reference image 610 which does not exist in defect footprint 815 lies between the two common boundaries CB intersected by defect boundary DB. If so, this defect is classified as a particle on the surface in step 1417. However, if a third common boundary CB3 lies inside defect boundary DB, this defect is classified as an embedded particle at step 1418.

Figure 13:
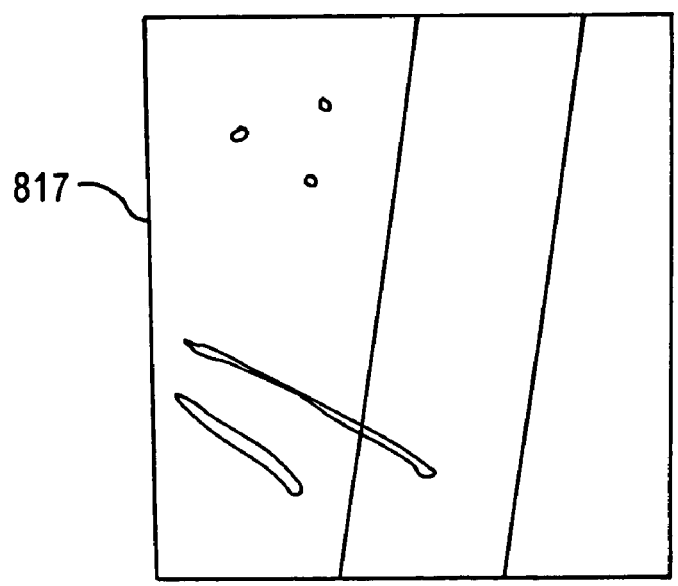
Figure 14A:
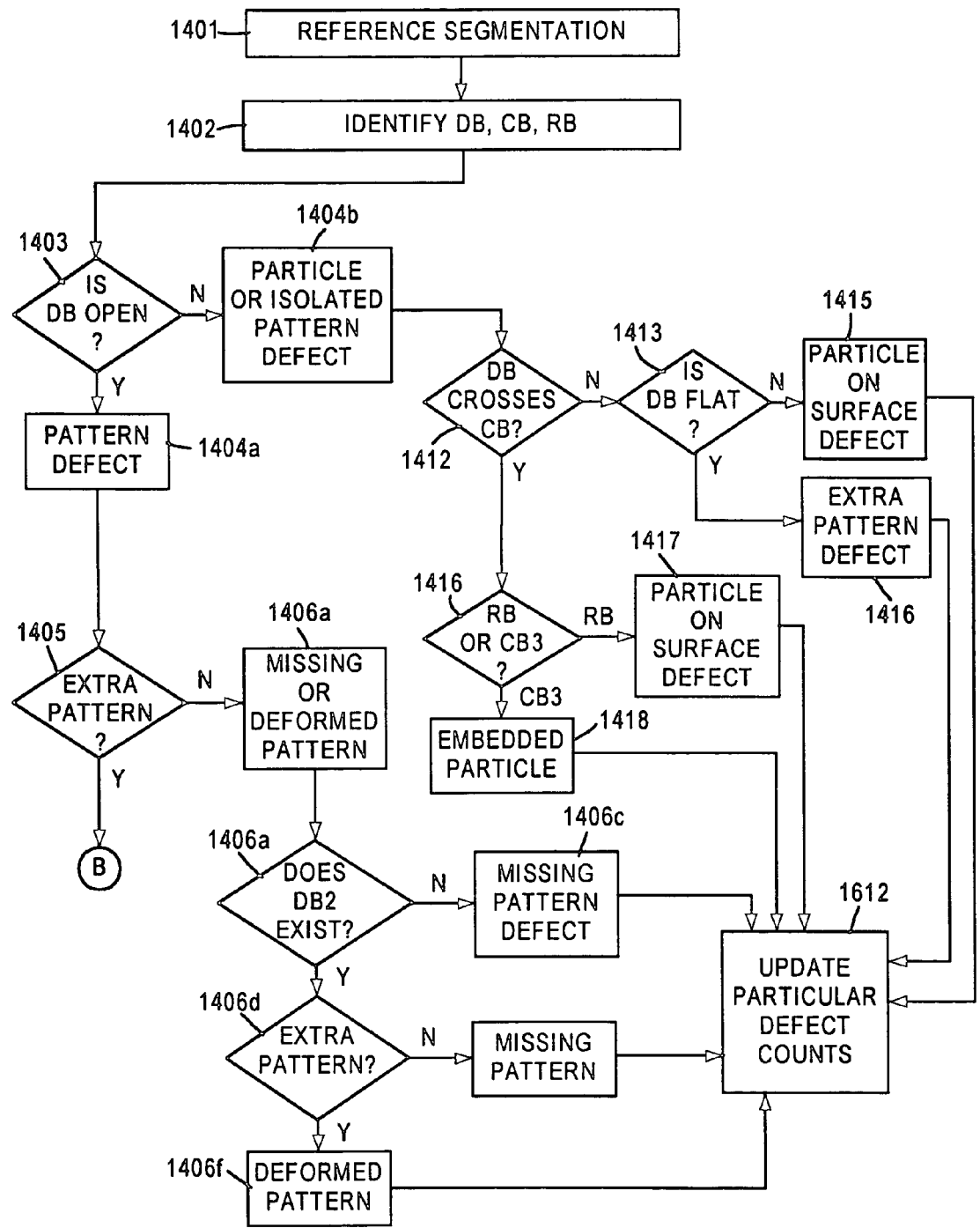
FIGS. 14a and 14b are a flow chart illustrating sequential steps of a second phase of a method according to the present invention.
Figure 14B:
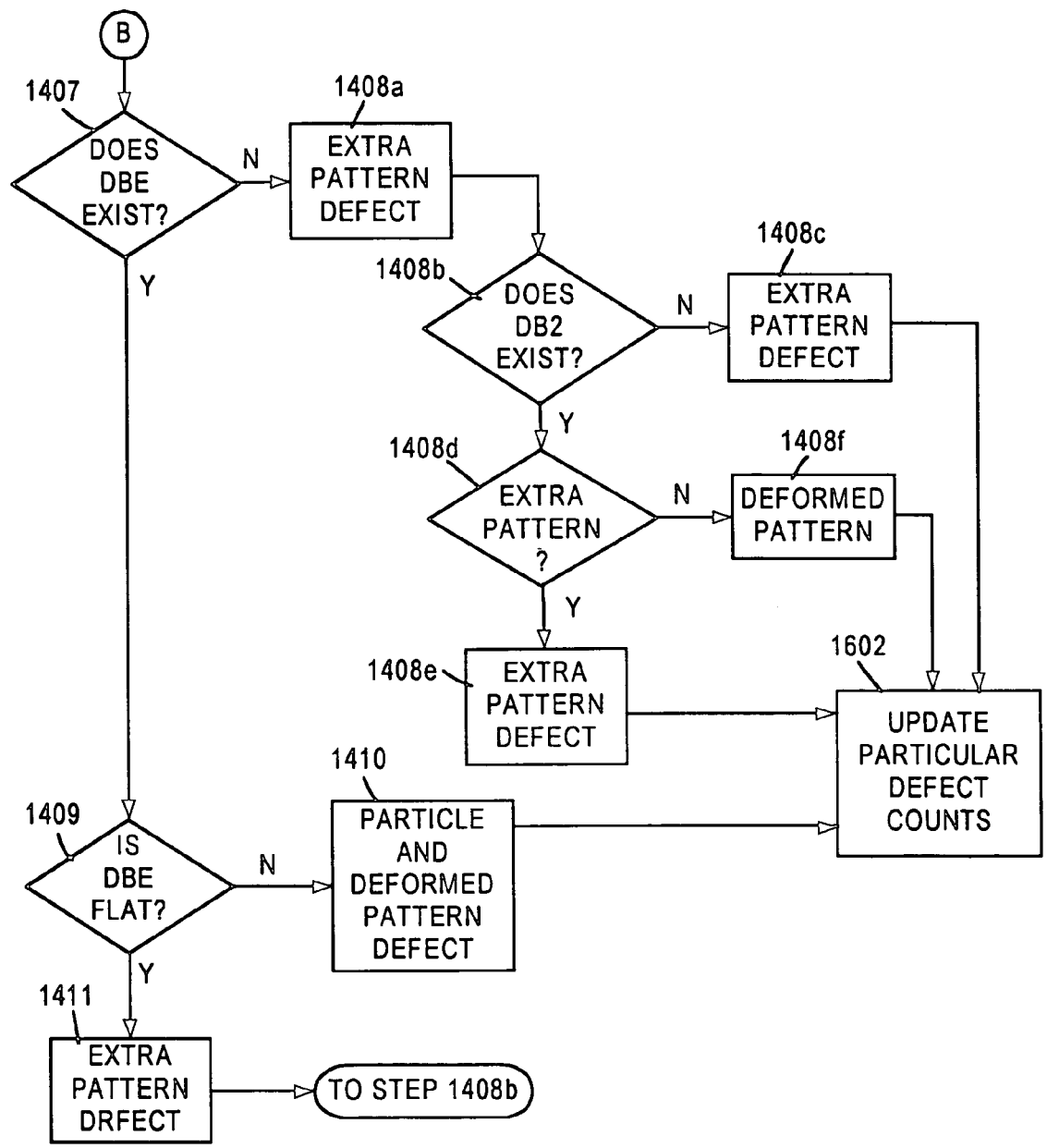

FIG. 13 shows a defect footprint 817 of the core class of craters and microscratches. A crater is a small gouge in the surface of the wafer. A microscratch is a very small scratch in the surface of the wafer.

Figure 18:
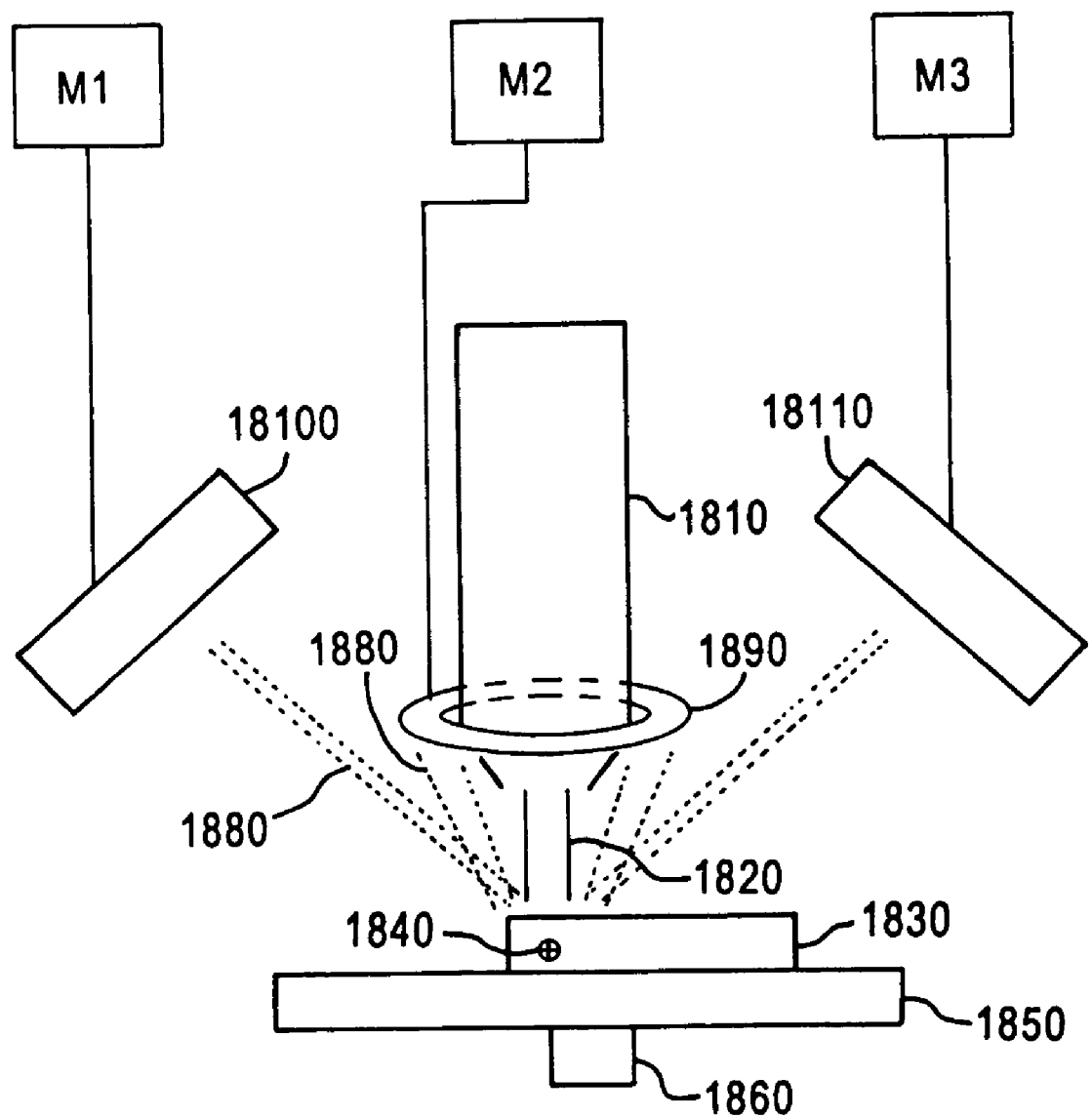
FIG. 18 is a schematic view of an SEM review station used to implement the present invention.
Figure 19A:
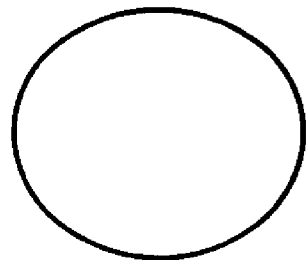
FIGS. 19(a)–19(c) show how a defect might be viewed using sensors of the apparatus of FIG. 18.
Figure 19B:
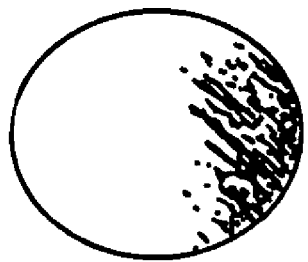

The detection of craters and microscratches as depicted in FIG. 13 and the particle defects depicted in FIGS. 12a and 12b is preferably accomplished using SEM multiple perspective imaging techniques, as disclosed in the Halavee and Litman patents. These techniques will now be briefly discussed with reference to FIGS. 18–20. FIG. 18 shows an SEM review station for determining depth information concerning defects in wafer structures using multiple SEM images. The SEM review station of FIG. 18 helps determine whether a defect is a protrusion, like a particle, or a recess, like a crater or microscratch.

The station shown in FIG. 18 comprises a plurality of sensors, also called "detectors". In this exemplary embodiment, there is a first sensor 1890 located centrally with respect to an SEM column 1810. First sensor 1890 is also referred to as an "inside the column" detector. There is a second sensor 18100 located to the left, and a third sensor 18110 located to the right, which are also referred to as "outside the column" detectors. The station of station of FIG. 18 takes three images of wafer 1830 mounted on stage 1850 at substantially the same time by directing electron beam 1820 at wafer 1830 and detecting electrons 1880 emitted from wafer 1830. The image produced by first sensor 1890 will be referred to as a first image; that from second sensor 18100 as a second image; and that from third sensor 18110 as a third image. However, these labels are for linguistic convenience only, and not meant to imply any order or sequence in image detection. Although the exemplary station shown in FIG. 18 has three stationary sensors 1890, 18100 and 18110, it is possible to employ less than three movable sensors, and move them to the three different positions of sensors 1890, 18100 and 18110 as required, since the images do not need to be taken simultaneously or in any particular order.

Due to the nature of SEM imaging, it will be appreciated that the first image has the perspective of electron beam 1820 (i.e., directly overhead) and appears as if the illumination is coming from first sensor 1890 (i.e., also directly overhead). The second image has the same identical perspective as the first image (i.e., the perspective of viewing from directly overhead), but appears as if the illumination is coming from second sensor 18100 (i.e., illumination from the left). The third image, like the second and first images, has an identical overhead perspective, but appears as if the illumination is coming from the right (i.e., from third sensor 18110).

The three images thus each provide different information with respect to bright and dim features of the area of defect 1840, and all from an identical perspective. Thus, a particular feature which appears flat when viewed from only directly overhead might look differently when viewed in connection with the other two images. It should be noted that the defects are extremely small, and therefore some defects may only prove detectable in one of the three images.

In essence, the first and third images provide greyscale shadow information useful for characterizing the defect, and the second image provides an overhead, substantially flat view.

One way to appreciate the advantage of this multiple perspective imaging technique is to consider a bump protruding from a planar surface. This bump represents a defect. Viewing this bump from directly overhead, with illumination from overhead, the bump may appear as a flat pattern or stain as drawn in FIG. 19(a). Such a result might obtain from an image produced by first sensor 1890. Based on this image alone, it would be difficult to characterize this defect as a flat circle, a protruding bump, or a pit.

In an image produced from second sensor 18100, the perspective of the viewer is still directly overhead, but with the illumination appearing to come from the left. Under these conditions, the bump may appear as having a brighter part on the left, and a dimmer part on the right, as drawn in FIG. 19(b). Thus, it may be determined that defect 1840 is a protrusion and not a pit.

In an image produced from third sensor 18110, the perspective of the viewer is still directly overhead, but with the illumination appearing to come from the right. Under these conditions, the bump may appear as having a brighter part on the right, and a dimmer part on the left, as drawn in FIG. 19(c). The determination of defect 1840 as a protrusion is thus confirmed. For example, to increase the level of confidence the greyscales produced from the second sensor can be compared to those produced by the third sensor.

Figure 19C:
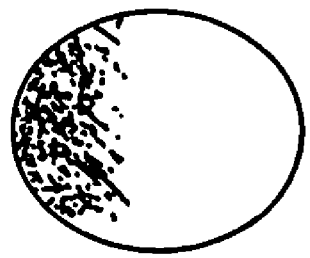

On the other hand, assume defect 1840 is a crater. The image produced by first sensor 1890 might still be as drawn in FIG. 19(a). The image produced by second sensor 18100 would show a darker area on the left and lighter area on the right of the pit, as shown in FIG. 19(c). Likewise, the image produced by the output of third sensor 18110 would show a darker area on the right and a lighter area on the left of the pit, as drawn in Fib. 19(b).

Figure 20A:
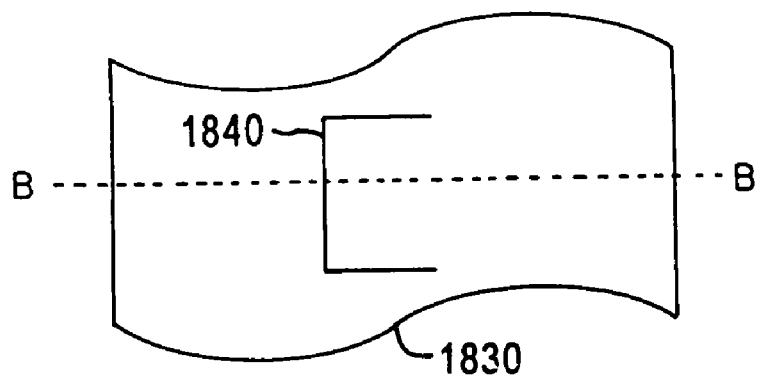
FIG. 20(a) depicts a microscratch on the surface of a wafer to be inspected.
Figure 20B:
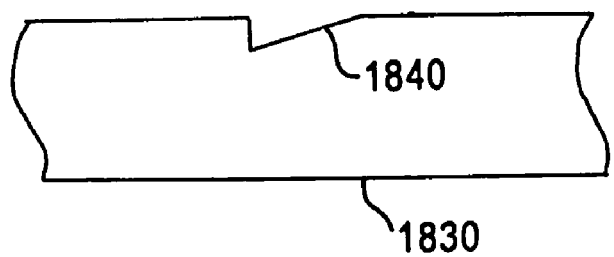
FIG. 20(b) is a cross-sectional view of the wafer of FIG. 20(a) taken along line B—B.

An example of the application of multiple perspective imaging to classify defects according to the present invention will now be discussed using FIGS. 20(a–e). FIG. 20(a) shows a part of wafer structure 1830 with defect 1840 as a microscratch. FIG. 20(b) shows a simplified cross-sectional view of wafer structure 1830 along reference line B—B. As shown in FIG. 20(b), the microscratch (i.e., defect 1840) is a vertical scratch having a substantially wall-like left side and a gently sloping right side. Although FIG. 20(a) shows upper and lower ends of this defect 1840, these are simply for reference and ease of illustration. It is much more likely that the microscratch has gently sloped ends.

Figure 20C:
FIGS. 20(c)–20(e) show how the microscratch might be viewed using the sensors of the apparatus of FIG. 18.

FIG. 20(c) shows how this defect 1840 might appear from first sensor 1890. Inasmuch as the illumination in the image provided from the data of first sensor 1890 appears to be from overhead, no shadows appear; the image from first sensor 1890 appears to be flat, and the microscratch appears to be only a linear feature. No depth information is available in this first image.

Figure 20D:

FIG. 20(d) shows how this defect 1840 might appear from second sensor 18100. The illumination appears to come from the left, and thus a shadow is caused by the substantially wall-like left side of the microscratch. Given the length of the shadow and the position of second sensor 18100, information as to the depth of the microscratch can be determined.

Figure 20E:
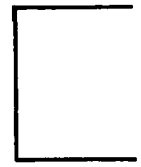

FIG. 20(e) shows how this defect 1840 might appear from third sensor 18110. The illumination appears to come from the right in such an image, but the gently sloping right side of the microscratch gives no shadow. Because of the inclination of the wall-like left side of the microscratch, the image provided from the output of third sensor 18110 appears flat, and defect 1840 appears to be only a linear feature.

In this example, the defect 1840 was substantially linear. Defects will rarely have so simple a structure, and so the information available from the three images taken together will normally reveal enough to detect and to characterize most defects.

To summarize, the multiple perspective imaging technique provides depth information to classify defects as craters and microscratches or particle defects using a plurality of images of a defect, with the images being simultaneously taken with different SEM sensors at different positions with respect to the defect. The plurality of images are compared. The differences in shading of the defect in the plurality of images are analyzed to determine the depth information. More specifically, the analysis determines whether the defect is flat, is a protrusion such as a particle defect as depicted in FIGS. 12a and 12b, or is a recess such as a crater or microscratch depicted in FIG. 13.

In another embodiment of the present invention, a monitor or set of monitors is provided, as shown in FIG. 18 as reference numerals M1–M3, to provide the user a display of each of the images produced by sensors 1890, 18100 and 18110. Visual access to the three different images is advantageous because the image from first sensor 1890 provides different information than the other sensors 18100, 18110.

First sensor 1890, located in the center of the station, contains information regarding the composition of matter of the defect and its surrounding area; i.e., it gives a visual indication of the presence of one or a plurality of different materials by the contrast of shading between different materials. For example, if two or more materials are present, this will be visually detectable because each material will be shaded differently. Second and third sensors 18100, 18110 produce images related to the topography of the defect, as discussed above, enabling the identification of a defect as a bump or a hole in the wafer surface. By displaying the images from all three sensors 1890, 18100, 18110, the user can see different aspects of the defect, thus enabling the user to determine that a defect is, for example, a bump on the wafer surface and that the bump is made of a different material than the surface.

The variant subclasses of defects carved out of the core classes are preferably provided as "on/off modules" or "building blocks" configurable by the user, so that as the user develops their process and determines which types of defects need to be identified and monitored, subclasses can be added or deleted.

Figure 15A:
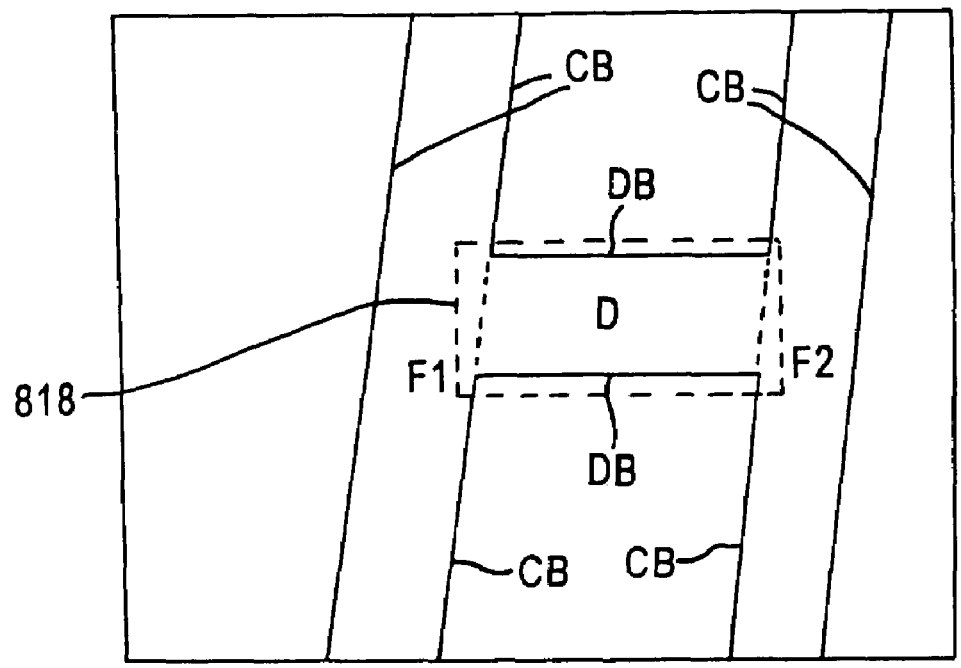
FIGS. 15a and 15b are representations of defects to be analyzed using the present invention.

For example, FIG. 15a illustrates a type of defect known as "bridging", which can be detected by the inventive methodology as required by the user as a subclass of the extra pattern core class of defect (e.g., after step 1408, 1410 or 1411 in FIG. 14b). Bridging, wherein two discrete patterns F1, F2 on the wafer surface are joined by an extra pattern D, almost certainly will cause short circuit failure of the completed device. Therefore, it is advantageous to be able to detect and classify this type of defect. Boundary analysis of defect footprint 818 determines that defect boundaries DB intersect at least one common boundary CB corresponding to each of the two discrete features F1, F2 in the reference image to classify the defect as bridging.

Figure 15B:
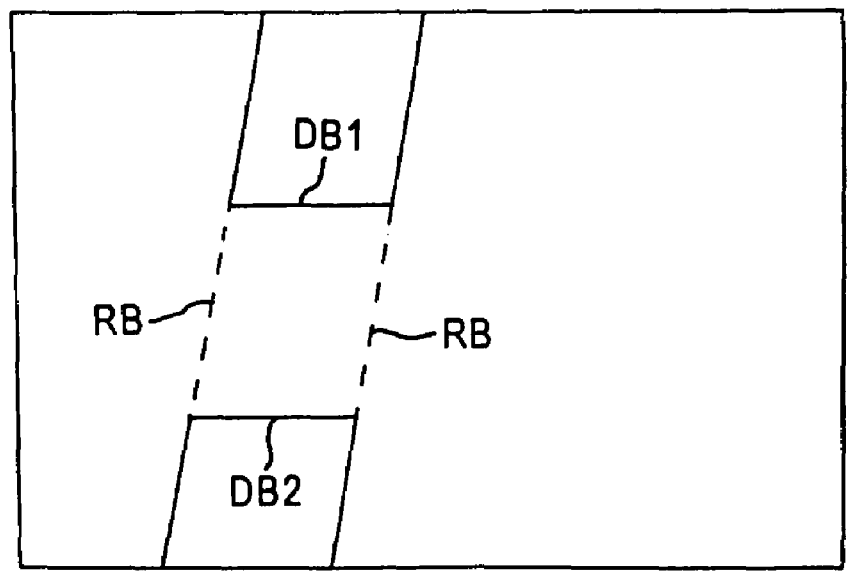

FIG. 15b depicts another optional subclass of the missing pattern core class known as a "broken line", which can be detected, e.g., after step 1406e in FIG. 14a detects a missing pattern defect, by analyzing the image of the area between DB 1 and DB2, for example by using techniques described in Litman et al. and Halavee et al. In other words, the feature with the missing pattern is measured to further determine to what extent the pattern is missing. A further example of the advantages of this capability is another subclass of the missing pattern core class called a "narrow pattern". Since a narrow pattern, such as depicted in FIG. 9, may cause device failure or inhibit device performance by increasing electrical resistance, a user may wish to determine if a pattern identified as a missing pattern defect is narrower than a prescribed width. By measuring the features in the areas around DB (e.g., defect footprint 812), the user can determine the width of the remaining pattern, and classify the defect as a narrow pattern defect if the width falls below a prescribed value.

Further subclassification of core classes of defects (i.e., subclass modules) can result from measuring the distance from one pattern to another to identify potential short circuits, such as measuring the distance from an extra pattern defect as shown in FIG. 8a, 8b or 10 to an adjacent pattern, then classifying the defect in a separate subclass if the distance is less than a prescribed value. Still further, particle defects as shown in FIGS. 11, 12a, and 12b can be measured and subclassified as "small particles" or "large particles" or particles above or below a prescribed area as desired by the user.

In another embodiment of the invention, the wafer surface can be optically imaged in order to obtain information not available from SEM images, such as the color of a layer under inspection, or the presence of a particle embedded in a layer of glass (e.g. silicon dioxide) which does not cause a bump on the surface of the glass large enough to be detected by an SEM. Thus, additional subclass modules may be added as required by the user to more thoroughly inspect the wafer.

In a third phase of the inventive methodology, as the possible defects indicated by the defect map are redetected, imaged and classified into core classes and subclasses of defects, a count is maintained of the total number of defects in each class. When the total number of defects in a specific one of the core classes or sub-classes is about equal to or exceeds a predetermined minimum acceptable number of that particular type of defect, an alarm signal may be generated to alert the user. In this way, "class density monitoring" of defects is carried out, allowing earlier warning of faults in a particular process, and shorter response time for corrective actions.

Figure 16:
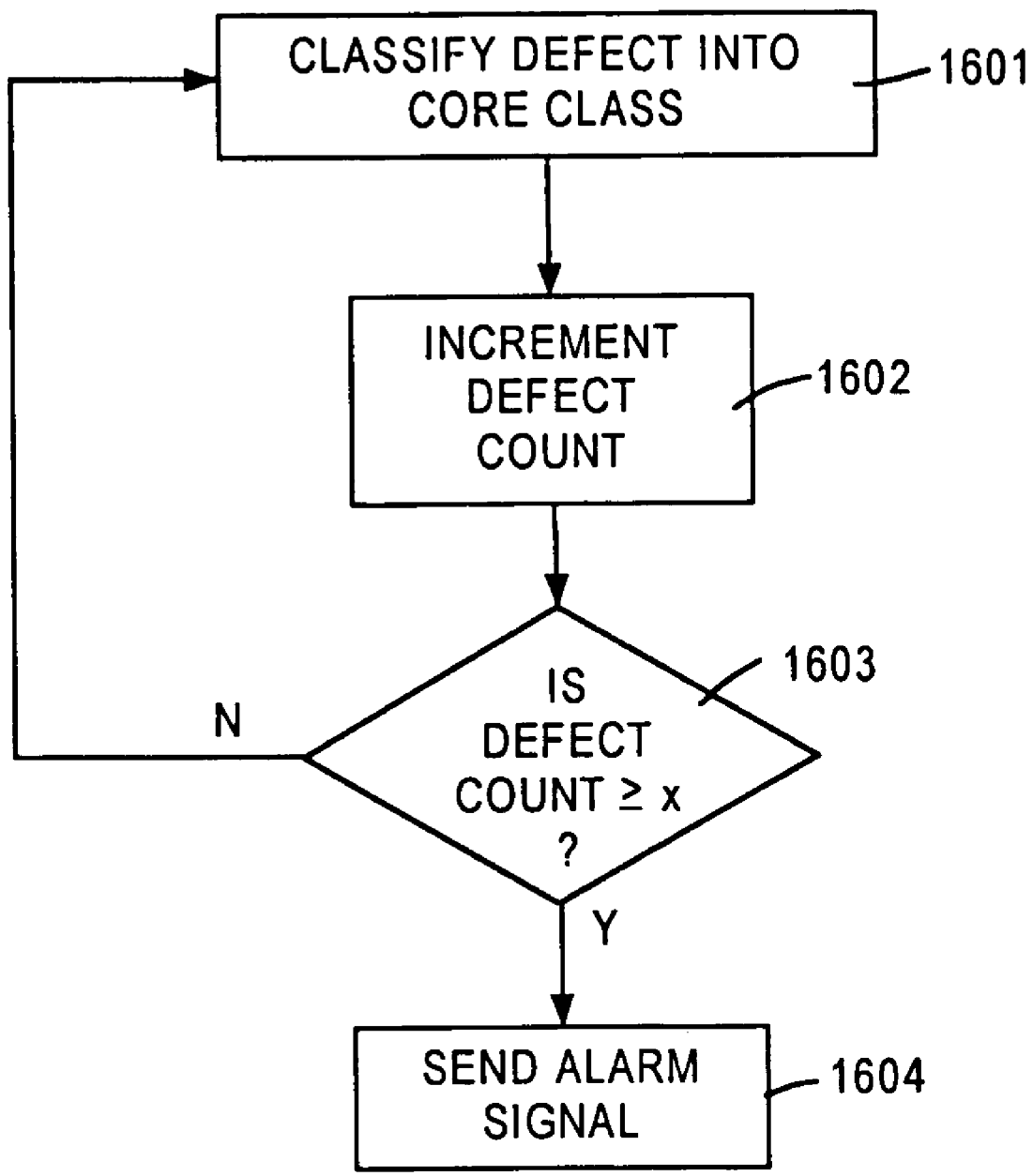
FIG. 16 is a flow chart illustrating sequential steps of a third phase of a method according to the present invention.

FIG. 16 is a flow chart of the third phase of the inventive methodology. After a defect is classified into core class A at step 1601, as performed according to the exemplary method depicted in FIGS. 14a and 14b, the defect count for that core class is incremented at step 1602 and then compared at step 1603 with a predetermined number x. If the defect count is greater than or equal to x, an alarm signal is sent to, for example, a display at step 1604. If the defect count is less than x, no alarm signal is sent. Alternately, the alarm signal may be replaced by an alert signal used to alert a control processor that automatically controls some aspect of a process to adjust the process to prevent the defect in future processing.

Figure 17:
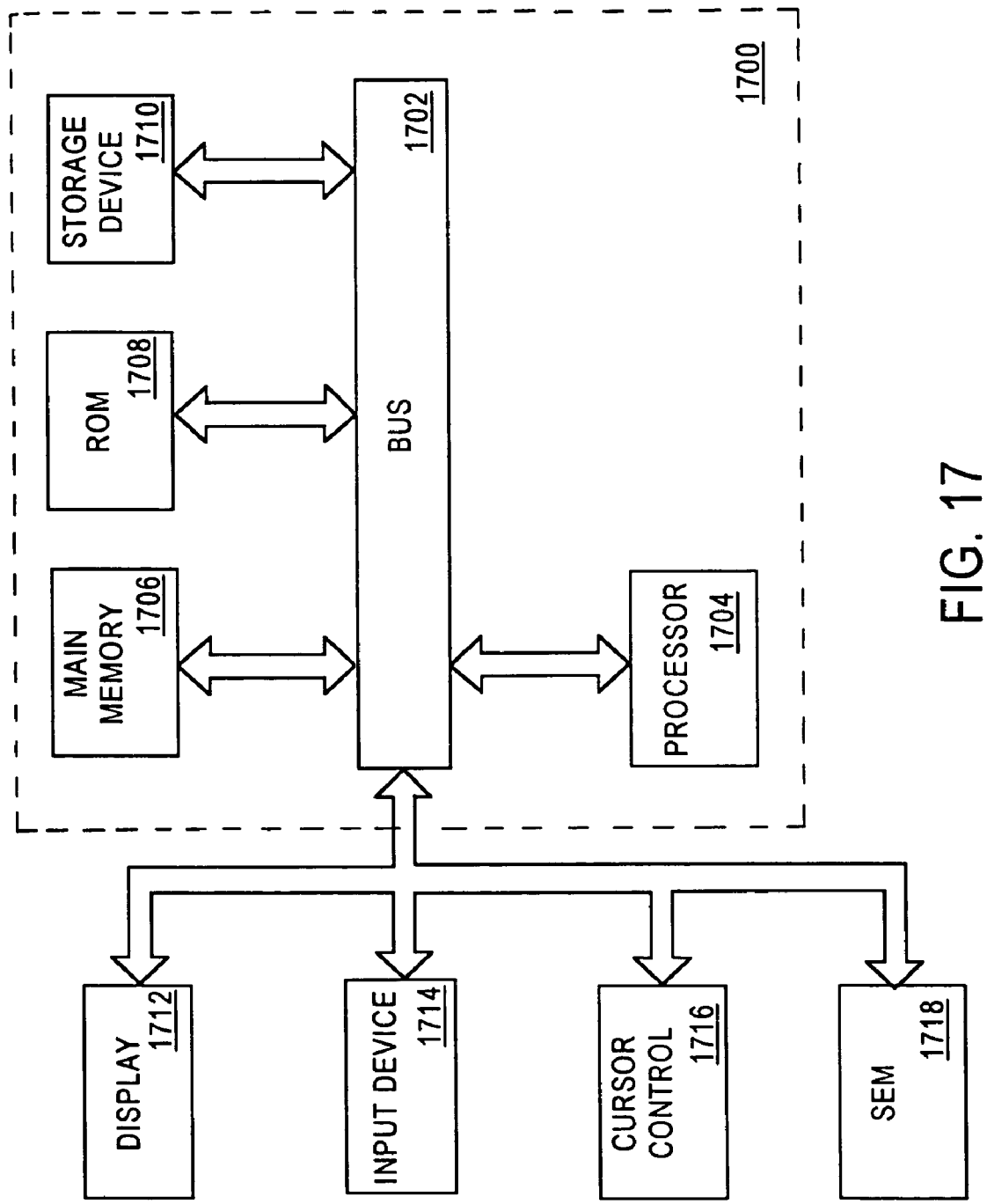
FIG. 17 is a block diagram that illustrates an embodiment of the invention.

FIG. 17 is a block diagram that illustrates an embodiment of the invention. A computer system 1700 includes a bus 1702 or other communication mechanism for communicating information, and a processor 1704 coupled with bus 1702 for processing information. Computer system 1700 also includes a main memory 1706, such as a random access memory (RAM) or other dynamic storage device, coupled to bus 1702 for storing information and instructions to be executed by processor 1704. Main memory 1706 also may be used for storing temporary variables or other intermediate information during execution of instructions to be executed by processor 1704. Computer system 1700 further includes a read only memory (ROM) 1708 or other static storage device coupled to bus 1702 for storing static information and instructions for processor 1704. A storage device 1710, such as a magnetic disk or optical disk, is provided and coupled to bus 1702 for storing information and instructions.

Computer system 1700 may be coupled via bus 1702 to a display 1712, such as a cathode ray tube (CRT), for displaying information to a computer user. An input device 1714, including alphanumeric and other keys, is coupled to bus 1702 for communicating information and command selections to processor 1704. Another type of user input device is cursor control 1716, such as a mouse, a trackball, or cursor direction keys for communicating direction information and command selections to processor 1704 and for controlling cursor movement on display 1712.

An SEM 1718 inputs data representative of images of a semiconductor wafer under inspection, as discussed above, to bus 1702. Such data may be stored in main memory 1706 and/or storage device 1710, and used by processor 1704 as it executes instructions. SEM 1718 may also receive instructions via bus 1702 from processor 1704.

The invention is related to the use of computer system 1700 for inspecting the surface of a semiconductor wafer for defects. According to one embodiment of the invention, inspection of the surface of a semiconductor wafer, including classification of surface defects, is provided by computer system 1700 in response to processor 1704 executing one or more sequences of one or more instructions contained in main memory 1706. Such instructions may be read into main memory 1706 from another computer-readable medium, such as storage device 1710. Execution of the sequences of instructions contained in main memory 1706 causes processor 1704 to perform the process steps described above. One or more processors in a multi-processing arrangement may also be employed to execute the sequences of instructions contained in main memory 1706. In alternative embodiments, hard-wired circuitry may be used in place of or in combination with software instructions to implement the invention. Thus, embodiments of the invention are not limited to any specific combination of hardware circuitry and software. The programming of the apparatus is readily accomplished by one of ordinary skill in the art provided with the flow chart of FIGS. 14a and 14b.

The term "computer-readable medium" as used herein refers to any medium that participates in providing instructions to processor 1704 for execution. Such a medium may take many forms, including but not limited to, non-volatile media, volatile media, and transmission media. Non-volatile media include, for example, optical or magnetic disks, such as storage device 1710. Volatile media include dynamic memory, such as main memory 1706. Transmission media include coaxial cable, copper wire and fiber optics, including the wires that comprise bus 1702. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, or any other medium from which a computer can read.

Various forms of computer-readable media may be involved in carrying out one or more sequences of one or more instructions to processor 104 for execution. For example, the instructions may initially be borne on a magnetic disk of a remote computer. The remote computer can load the instructions into its dynamic memory and send the instructions over a telephone line using a modem. A modem local to computer system 1700 can receive the data on the telephone line and use an infrared transmitter to convert the data to an infrared signal. An infrared detector coupled to bus 1702 can receive the data carried in the infrared signal and place the data on bus 1702. Bus 1702 carries the data to main memory 1706, from which processor 1704 retrieves and executes the instructions. The instructions received by main memory 1706 may optionally be stored on storage device 1710 either before or after execution by processor 1704.

The inventive semiconductor wafer inspection technique enables defects to be separately and reliably classified as particle or pattern defects, and as on-surface or below-surface (embedded) defects. It also provides early quantification and notification of these meaningfully classified defects, thereby facilitating investigation of the causes of the defects, and enabling early corrective action to be implemented. Thus, the present invention contributes to the maintenance of production throughput. Moreover, the inventive methodology classifies defects by imaging the wafer surface and performing boundary analysis and/or topographical measurement of its features, and so does not require examples of defect images for each class prior to being operational. Therefore, unlike prior art defect classification systems, the present invention can be used during the start-up and ramp-up of a production line.

The present invention is applicable to the inspection of any semiconductor wafer, and is especially useful for in-process inspection of semiconductor wafers during manufacture of high density semiconductor devices with submicron design features.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, as one having ordinary skill in the art would recognize, the present invention can be practiced without resorting to the details specifically set forth. In other instances, well known processing structures have not been described in detail, in order not to unnecessarily obscure the present invention.

Only the preferred embodiment of the invention and but a few examples of its versatility are shown and described in the present disclosure. It is to be understood that the invention is capable of use in various other combinations and environments and is capable of changes or modifications within the scope of the inventive concept as expressed herein.

What is claimed is:

1. A method of automatically classifying defects on the surface of an article, which method comprises at least:
    imaging the surface;
    classifying each of the defects as being in one of a predetermined number of invariant core classes of defects;
    determining a total number of defects in each of the core classes; and
    generating an alarm signal when the total number of defects in a specific one of the core classes is equal to or greater than a first predetermined number.

2. The method according to claim 1, wherein the core classes of defects comprise a missing pattern on the surface, an extra pattern on the surface, a particle on the surface, a particle embedded in the surface, and microscratches on the surface.

3. The method according to claim 1, comprising imaging the surface with a scanning electron microscope.

4. The method according to claim 1, comprising further classifying one of the defects as being in one of an arbitrary number of variant subclasses of at least one of the invariant core classes.

5. The method according to claim 4, comprising classifying a plurality of defects on the surface of the article; and
    determining a total number of defects in each of the subclasses.

6. The method according to claim 5, comprising generating an alarm signal when the total number of defects in a specific one of the subclasses is about equal to or greater than a second predetermined number.

7. A computer-readable medium bearing instructions for automatically classifying defects on the surface of an article, said instructions, when executed, being arranged to cause one or more processors to perform the steps of:
    imaging the surface;
    classifying each of the defects as being in one of a predetermined number of invariant core classes of defects;
    determining a total number of defects in each of the core classes; and
    generating an alarm signal when the total number of defects in a specific one of the core classes is about equal to or greater than a first predetermined number.

8. The computer-readable medium according to claim 7, wherein the core classes of defects comprise a missing pattern on the surface, an extra pattern on the surface, and a particle on the surface.

9. The computer-readable medium according to claim 7, wherein the instructions, when executed, are arranged to cause the one or more processors to perform the step of imaging the surface with a scanning electron microscope.

10. The computer-readable medium according to claim 7, wherein the instructions, when executed, are arranged to cause the one or more processors to perform the step of classifying one of the defects as being in one of an arbitrary number of subclasses of at least one of the invariant core classes, the subclasses being of arbitrarily defined defects.

11. The computer-readable medium according to claim 10, wherein the instructions, when executed, are arranged to cause the one or more processors to perform the steps of:
    classifying a plurality of defects on the surface of the article; and
    determining a total number of defects in each of the subclasses.

12. The computer-readable medium according to claim 11, wherein the instructions, when executed, are arranged to cause the one or more processors to perform the step of generating an alarm signal when the total number of defects in a specific one of the subclasses is about equal to or greater than a second predetermined number.

13. The computer-readable medium according to claim 7, wherein the instructions, when executed, are arranged to cause the one or more processors to perform the step of imaging by acquiring a plurality of images using a plurality of spaced-apart detectors.

14. The computer-readable medium according to claim 13, wherein the instructions, when executed, are arranged to cause the one or more processors to acquire the images by causing the detectors to collect electrons.

15. An apparatus for classifying defects on the surface of an article, comprising:
- an imager to produce an image of the defect and a reference image;
- a storage device to store the defect image and the reference image;
- a comparator to compare the defect image and the reference image;
- a processor to classify the defect as being in one of a predetermined number of invariant core classes of defects;
- a first counter for counting the number of defects in each of the core classes; and
- a first signal generator for generating an alarm signal when the total number of defects in a specific one of the core classes is about equal to or greater than a first predetermined number.

16. The apparatus of claim 15, wherein the imager is a scanning electron microscope (SEM).

17. The apparatus of claim 16, further comprising a plurality of spaced-apart detectors and a monitor to display images produced by the plurality of detectors.

18. The apparatus of claim 16, wherein the SEM comprises an SEM column, wherein a first one of the plurality of detectors is disposed inside the SEM column and a second one of the plurality of detectors is disposed outside the SEM column.

19. The apparatus of claim 18, further comprising a first monitor for displaying an image produced by the first detector, and a second monitor for displaying an image produced by the second detector.

20. The apparatus of claims 15, wherein the storage device is a digital storage device.

21. The apparatus of claim 15, further comprising of processor for classifying the defect as being in one of arbitrary number of subclasses of at least one of the invariant core classes, the subclasses being of arbitrarily defined defects.

22. The apparatus of claim 21, further comprising a second counter for counting the number of defects in each of the subclasses and a second signal generator for generating an alarm signal when the total number of defects in a specific one of the subclasses is about equal to or greater than a second predetermined number.

* * * * *